Figure 1:
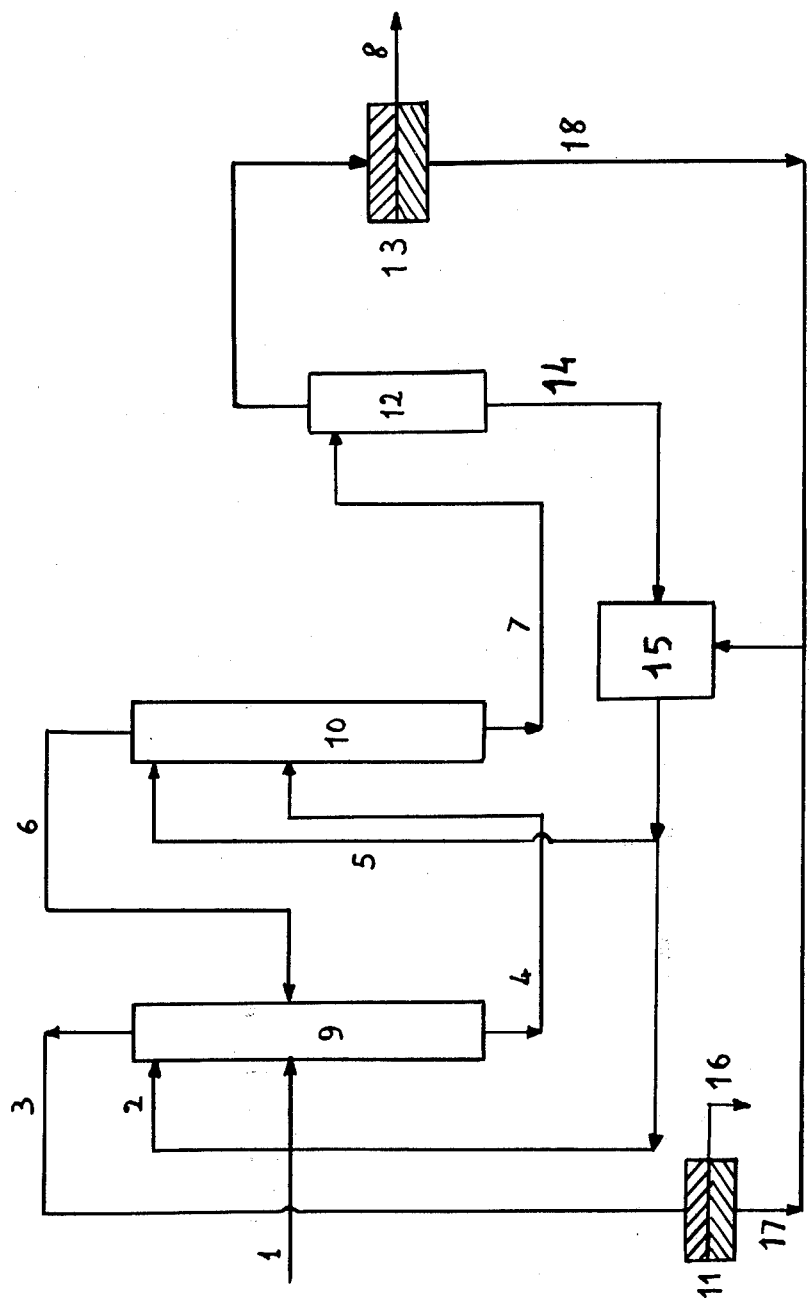

United States Patent [19]

Ginnasi et al.

[11] 3,953,300
[45] Apr. 27, 1976

[54] PROCESS FOR SEPARATING A HIGH PURITY VINYL AROMATIC HYDROCARBON FROM HYDROCARBON MIXTURES CONTAINING THE SAME

[75] Inventors: Alessandro Ginnasi, San Donato Milanese; Alessandro Vetere, Milan; Pierantonio Martera, San Donato Milanese, all of Italy

[73] Assignee: Snam Progetti, S.p.A., San Donato Milanese, Italy

[22] Filed: July 11, 1975

[21] Appl. No.: 595,291

Related U.S. Application Data

[63] Continuation of Ser. No. 417,377, Nov. 19, 1973, abandoned.

[30] Foreign Application Priority Data

Nov. 29, 1972  Italy .................................. 32208/72

[52] U.S. Cl. ................................. 203/53; 203/58; 203/82; 203/39; 260/669 A; 208/313; 208/326
[51] Int. Cl.² ...................... B01D 3/40; C07C 15/10
[58] Field of Search .................... 203/53, 39, 54, 82, 203/58; 260/669 A; 208/313, 325, 326

[56] References Cited
UNITED STATES PATENTS

| | | | |
|---|---|---|---|
| 2,465,715 | 3/1949 | Engel | 203/53 |
| 2,465,718 | 3/1949 | Engel | 203/53 |
| 2,467,198 | 4/1949 | Greene | 203/53 |
| 3,018,228 | 1/1962 | Cornell | 260/669 A |
| 3,210,259 | 10/1965 | Cornell | 203/58 |
| 3,328,267 | 6/1967 | Muller | 260/669 A |
| 3,434,936 | 3/1969 | Luther et al. | 203/58 |
| 3,551,327 | 12/1970 | Kelly et al. | 208/313 |
| 3,720,605 | 3/1973 | Pareb | 208/313 |
| 3,763,037 | 10/1973 | Thompson | 208/313 |
| 3,784,626 | 1/1974 | Gennasi et al. | 208/313 |

*Primary Examiner*—Wilbur L. Bascomb, Jr.
*Attorney, Agent, or Firm*—Ralph M. Watson

[57] ABSTRACT

Styrene of exceptional purity is separated from a mixture of hydrocarbons including it, xylenes, saturated and olefinic hydrocarbons and ethyl benzene by means of a two-step extractive distillation process through the use of a high boiling polar solvent such as N-formyl morpholine in admixture with an amount of water in the range of from 1% to 30% by weight.

1 Claim, 1 Drawing Figure

PROCESS FOR SEPARATING A HIGH PURITY VINYL AROMATIC HYDROCARBON FROM HYDROCARBON MIXTURES CONTAINING THE SAME

This is a continuation of application Ser. No. 417,377 filed Nov. 19, 1973 now abandoned.

The present invention relates to a process for separating a vinyl aromatic hydrocarbon of high purity hydrocarbon from hydrocarbon mixtures containing the same. More particularly the the present invention relates to a process for separating a vinyl aromatic hydrocarbon of high purity from hydrocarbon mixtures containing the same by extractive distillation in the presence of suitable water containing solvents.

Still more particularly the present invention relates to a process for separating styrene of high purity from hydrocarbon mixtures containing the same by extractive distillation in the presence of suitable water containing solvents. In the following description for the sake of simplicity we shall refer only to the separation from hydrocarbon mixtures of styrene, even though the process according to the invention is suitable to the separation of any vinyl aromatic hydrocarbon.

The starting mixtures from which styrene can be separated with particular advantage are the ones obtained by steam cracking of naphta.

Many processes have been developed for separating styrene from hydrocarbon mixtures containing it.

The most recent processes are based on the extractive distillation of the hydrocarbon mixtures in the presence of suitable solvents.

It is to be noted that the temperature has to be kept very low to styrene polymerization due to a thermal action.

In the specific case of styrene it is necessary to work at temperatures at least lower than 110°C; in fact up to this temperature the starting polymerization rate, expressed by % per hour, is limited to values lower than or at most equal to 1%.

Since the solvents having the highest selective power are the ones boiling at high temperature, to maintain a distillation temperature lower than 110° in the presence of the same it is necessary to work under very high vacuum and this unavoidably involves prohibitive costs.

We have surprisingly found that the addition of water to high boiling polar solvents or mixtures of solvents selected among aldo- and keto-morpholines, in particular N-formyl morpholine, N-methyl pyrrolidone and sulpholane having a water concentration ranging from 1% to 30% by weight based on the mixture and preferably from 5 to 20% by weight, does not lower in a significant way the solvent power.

By working with such aqueous solvents is therefore possible to maintain temperatures lower than 110°C in the extractive distillation columns, limiting in a remarkable way the vacuum, without any marginal drawback.

Furthermore it is known that the addition of water to the aforesaid solvents or solvent mixtures allows an increase in the selectivity of the solvent itself. The effect of water with respect to the increase of the working pressure of the extractive distillation columns is pointed out in the enclosed table 1 wherein there are reported for anhydrous solvents and for solvents with various water percentages the working pressures which can be reached when the column bottom temperature is 100°C.

The amount of xylenes present is constant in the various tests and equal to 10% by weight.

TABLE 1

|  |  |  | t (°C) | Pressure (mmHg) |
|---|---|---|---|---|
| N-methyl pyrrolidone | (anhydrous) | + 10% xylenes | 100 | 140 |
| " | (+5% H₂O) + | " | 100 | 285 |
| " | (+10% H₂O) + | " | 100 | 410 |
| " | (+20% H₂O) + | " | 100 | 560 |
| N-formyl morpholine | (anhydrous) | + 10% Xylenes | 100 | 50 |
| " | (+5% H₂O) + | " | 100 | 290 |
| " | (+20% H₂O) + | " | 100 | 700 |
| Sulpholane | (anhydrous) | + 10% xylenes | 100 | 40 |
| " | (+5% H₂O) + | " | 100 | 435 |
| " | (+20% H₂O) + | " | 100 | 750 |

The process which is the subject of the present invention can be carried out according to a scheme which, without being restrictive, comprises the following steps (see FIG. 1):

1. Feeding the hydrocarbon mixture containing styrene (obtained by steam cracking) to the intermediate zone of a first extractive distillation column to which the solvent-water mixture is fed in proximity to the top.

2. Withdrawing from the top of the first extractive distillation column a hydrocarbon stream comprising essentially most of xylenes as well as saturated and olefinic hydrocarbons, ethyl benzene and water.

3. Discharging from the bottom of the first extractive distillation column a stream constituted essentially by styrene, o-xylene and the extraction solvent.

4. Feeding the stream of point (3) to a second extractive distillation column into which the solvent-water is introduced in proximity to the top.

5. Withdrawing from the top of the 2nd extractive distillation column a stream constituted by water, styrene and o-xylene which stream is recycled to the 1st extractive distillation column in proximity to the primary feed.

6. Discharging from the bottom of the second extractive distillation column a stream constituted essentially by styrene, solvent and water.

7. Feeding the stream of point (6) to a stripper in order to obtain as overhead product, after separation of water, styrene and as bottom product the solvent which is recycled to the extractive distillation columns in proximity to the top.

Some examples will now be given to illustrate in a better way the invention without limiting the same.

EXAMPLE 1

Reference is made to FIG. 1.

We fed to column (9) a stream (1) of 100 kg/h of a C₈ cut having the following composition:

| | | |
|---|---|---|
| C₈ saturated and olefinic hydrocarbons | 3.5 | kg/h |
| O-xylene | 17.0 | " |
| m-xylene ⎤ p-xylene ⎦ | 43.1 | " |
| ethylbenzene | 8.6 | " |
| styrene | 27.8 | " |

The conditions were the following ones:

| | | |
|---|---|---|
| Overhead pressure | = | 140 mm Hg |
| Reflux ratio | = | 5 |
| Number of plates | = | 80 |
| Bottom temperature | = | 100 °C |

To the head zone of column (9) we fed though line (2) the extraction solvent constituted by N-formyl morpholine containing 5% of H₂O at a rate 15 times higher than feed (1).

As overhead product we withdraw water and a strem of organic raffinate having the following composition:

| | | |
|---|---|---|
| C₈ saturated and olefinic hydrocarbons | 3.5 | kg/h |
| O-xylene | 16.85 | " |
| m-xylene ⎤ p-xylene ⎦ | 43.10 | " |
| ethyl benzene | 8.60 | " |
| styrene | 0.30 | " |

The stream was sent to a separator (decanter) (11) for separating from the organic raffinate (16) water (17) which was used again in a suitable point of the cycle.

From the bottom of column (9) we discharged (line 4) a stream constituted by solvent and a hydrocarbon fraction having the following composition:

| | |
|---|---|
| styrene: | 38.28 kg/h |
| o-xylene | 6.80 " |

This last stream was sent to the extractive distillation column (10) working at the following conditions:

| | | |
|---|---|---|
| overhead pressure | = | 160 mm Hg |
| reflux ratio | = | 2.5 |
| number of plates | = | 60 |
| bottom temperature | = | 100 °C |

To the head zone of column (10) we fed through line (5) the extraction solvent constituted by N-formyl morpholine with 5% H₂O at a rate equal to 1.5 times the one of the feeding.

As overhead product (line 6) we removed water and a stream of organic raffinate having the following composition:

| | |
|---|---|
| styrene | 10.78 kg/h |
| O-xylene | 6.60 " |

This last stream was fed back to column (9) at the same height of the primary feed (1).

From the bottom of column (10) we discharged a stream (7) constituted by the solvent and a hydrocarbon fraction having the following composition:

| | |
|---|---|
| styrene | 27.50 kg/h |
| O-xylene | 0.05 " |

Stream (7) was fed to stripper (12) in order to separate the hydrocarbons therein contained from the solvent. The solvent was discharged from the bottom through line (14) and reused in the cycle, after mixing in (15) with the water recovered in the various process steps (17 and 18) in order to keep constant the solvent concentration.

According to requirements a portion of the water (17 and 18) recovered from the separators (decanters) was fed to the bottom zone of the extractive distillation columns (9) and (10) or to other points of the cycle.

The hydrocarbons recovered as overhead product and separated from water in (13) were sent through line (8) to a conventional rectification for further purification.

Styrene is obtained at a purity of about 99.8%.

EXAMPLE 2

Reference is made to FIG. 1.

To column (9) we fed stream (1) having the following composition based on 100 kg/h:

| | |
|---|---|
| C₆ hydrocarbons | 51.08 kg/h |
| C₇ hydrocarbons | 27.40 " |
| C₈ saturated and olefinic hydrocarbons, ethylbenzene, m-xylene, p-xylene | 11.37 " |
| Styrene | 6.30 " |
| O-Xylene | 3.85 " |

The working conditions were the following ones:

| | | |
|---|---|---|
| Overhead pressure | = | 140 mm Hg |
| Reflux ratio | = | 5 |
| Number of plates | = | 80 |
| Bottom temperature | = | 100 °C |

To the head zone of column (9) the extraction solvent was fed through line (2), said solvent being constituted by N-formyl morpholine containing 5% H₂O at a rate equal to 30 times the one of the feed (1).

From the top we discharged (line 3) H₂O and a stream of hydrocarbon raffinate having the following composition:

| | |
|---|---|
| C₆ hydrocarbons | 51.08 kg/h |
| C₇ " | 27.40 " |
| C₈ saturated and olefinic hydrocarbons, ethylbenzene, m-xylene, p-xylene | 11.36 " |
| O-xylene | 3.83 " |
| styrene | 0.06 " |

This stream was sent to separator (decanter) (14) for separating from the organic raffinate (16) water (17) which was used again in a suitable point of the cycle.

From the bottom of column (9) we discharged (line 4) a stream constituted by solvent and a hydrocarbon fraction of the following composition:

| | | |
|---|---|---|
| O-xylene | = | 2.35 kg/h |
| styrene | = | 10.02 " |

Said last stream was sent to the extractive distillation column (10) working at the following conditions:

| | | |
|---|---|---|
| Over-head pressure | | 160 mm Hg |
| reflux ratio | | 1.6 |
| number of plates | | 66 |
| bottom temperature | | 100 °C |

The extraction solvent constituted by N-formyl morpholine with 5% water at a rate equal to 1.5 times the one of the feed was feed through line (5) to the head zone of column (10).

As overhead product (line 6) we withdraw water and a stream of organic raffinate of the following composition:

| | |
|---|---|
| O-xylene | 2.31 kg/h |
| styrene | 3.78 " |

This last stream was sent back to column (9) at the same height of the primary feed (1).

From the bottom of column (10) we discharged a stream (7) constituted by solvent and a hydrocarbon fraction of the following composition:

| | |
|---|---|
| O-xylene | 0.01 kg/h |
| styrene | 6.24 " |

Stream (7) was fed to stripper (12) for separating the hydrocarbons contained therein from the solvent. The solvent was discharged from the bottom through line (14) and was re-used in the cycle, after mixing in (15) with the water recovered from the various process steps (streams 17 and 18) in order to maintain constant its concentration in the solvent.

According to requirements a portion of the water of streams (17) and (18) was fed to the bottom zones of the extractive distillation columns (9) and (10) or to other points of the cycle.

The hydrocarbons recovered as overhead product and separated from water in (13) were sent through line (8) to a conventional rectification for a further purification.

Styrene is obtained with a purity of about 99.8%.

EXAMPLE 3

Reference is made to FIG. 1.

We fed a stream constituted by a $C_8$ cut equal to the one of example 1. The used solvent was N-methyl pyrrolidone with 5% $H_2O$, its rate being 15 times higher than the one of the feed; the working conditions of column (9) were the following ones:

| | |
|---|---|
| overhead pressure | 140 mm Hg |
| reflux ratio | 5 |
| number of plates | 80 |
| bottom temperature | 100 °C |

The working conditions of columns (10) were:

| | |
|---|---|
| overhead pressure | 160 mm Hg |
| reflux ratio | 2.5 |
| number of plates | 60 |
| bottom temperature | 100 °C |

The extracted styrene had a purity of about 99.8%.

All remaining conditions omitted in this example were similar to the ones of the examples 1 and 2.

EXAMPLE 4

Reference is made to FIG. 1.

We fed a stream constituted by a $C_8$ cut like the one of example 1. The used solvent was sulpholane with 5% $H_2O$ at a rate 15 times higher than the one of the feed; the working conditions of column (9) were the following ones:

| | |
|---|---|
| overhead pressure | 280 mm Hg |
| reflux ratio | 5 |
| number of plates | 80 |
| bottom temperature | 100 °C |

The working conditions of column (10) were the following ones:

| | |
|---|---|
| overhead pressure | 300 mm Hg |
| reflux ratio | 2.5 |
| number of plates | 60 |
| bottom temperature | 100 °C |

The extracted styrene had a final purity of about 99.8%.

All remaining conditions omitted in this example were similar to the ones of examples 1 and 2.

What we claim is:

1. Process for separating styrene from a hydrocarbon mixture containing styrene, xylenes including o-xylene, saturated and olefinic hydrocarbons and ethyl benzene by means of extractive distillation with N-formyl morpholine as extraction solvent in admixture with an amount of water in the range of from 5% to 20% by weight, comprising the following steps:
    1. feeding said hydrocarbon mixture to the intermediate zone, and feeding said solvent-water mixture in proximity to the top, of a first extractive distillation column;
    2. withdrawing from the top of said first extractive distillation column a hydrocarbon stream constituted essentially of most of said xylenes, saturated and olefinic hydrocarbons, ethyl benzene and water;
    3. discharging from the bottom of said first extractive distillation column a stream constituted essentially of styrene, o-xylene and extraction solvent;
    4. feeding the stream from step (3) to a second extractive distillation column and feeding the solvent-water to said second extractive distillation column in proximity to its top;
    5. withdrawing from the top of said second extractive distillation column a stream constituted of water, styrene and o-xylene and recycling the same to the first extractive distillation column in proximity to the primary feed;
    6. discharging from the bottom of the second extractive distillation column a stream constituted essentially of styrene, solvent and water; and
    7. feeding the stream from step (6) to a stripper and withdrawing styrene and water as overhead product, and, as bottom product, solvent for recycle to said extractive distillation columns; and
    8. separating the water from the styrene in the overhead product of step (7) by decantation and recovering said styrene.

* * * * *